(12) United States Patent
Westphal

(10) Patent No.: US 9,144,400 B2
(45) Date of Patent: Sep. 29, 2015

(54) METHOD AND DEVICE FOR MEASURING DISSOLVED SUBSTANCES IN HUMAN OR ANIMAL INTRAOCULAR FLUID

(71) Applicant: Carl Zeiss AG, Oberkochen (DE)

(72) Inventor: Peter Westphal, Jena (DE)

(73) Assignee: Carl Zeiss AG, Oberkochen (DE)

( * ) Notice: Subject to any disclaimer, the term of this patent is extended or adjusted under 35 U.S.C. 154(b) by 0 days.

(21) Appl. No.: 14/243,594

(22) Filed: Apr. 2, 2014

(65) Prior Publication Data

US 2014/0249392 A1   Sep. 4, 2014

Related U.S. Application Data

(63) Continuation of application No. 12/921,747, filed as application No. PCT/DE2009/000289 on Mar. 2, 2009, now Pat. No. 8,755,855.

(30) Foreign Application Priority Data

Mar. 10, 2008  (DE) .......................... 10 2008 013 821

(51) Int. Cl.
  *A61B 5/1455*  (2006.01)
  *A61B 5/145*   (2006.01)
  *A61B 3/10*    (2006.01)

(52) U.S. Cl.
  CPC ............. *A61B 5/14507* (2013.01); *A61B 3/102* (2013.01); *A61B 5/14558* (2013.01)

(58) Field of Classification Search
  CPC . A61B 5/14558; A61B 5/14507; A61B 3/102
  See application file for complete search history.

(56) References Cited

U.S. PATENT DOCUMENTS

| | | | |
|---|---|---|---|
| 3,963,019 A | 6/1976 | Quandt | |
| 5,433,197 A | 7/1995 | Stark | |
| 5,535,743 A | 7/1996 | Backhaus et al. | |
| 5,882,301 A | 3/1999 | Yoshida | |
| 6,226,089 B1 | 5/2001 | Hakamata | |

(Continued)

FOREIGN PATENT DOCUMENTS

| DE | 42 43 142 A1 | 6/1994 |
|---|---|---|
| DE | 693 08 438 T2 | 10/1997 |

(Continued)

OTHER PUBLICATIONS

Application and File history for U.S. Appl. No. 12/921,747, filed Jan. 13, 2011. Inventor: Peter Westphal.

*Primary Examiner* — Eric Winakur
(74) *Attorney, Agent, or Firm* — Patterson Thuente Pedersen, P.A.

(57) ABSTRACT

Non-invasive optical measurement of glucose and other dissolved substances in human or animal intraocular fluid. A method takes advantage of the fact that the wave dependence of optical activity is fundamentally different from corneal birefringence. The optical activity of substances dissolved in the intraocular fluid, such as glucose, lactate, ascorbic acid or amino acids, is scaled as a first approximation with the reciprocal value of the wavelength square. In contrast, corneal birefringence is scaled with the reciprocal value of the wavelength and therefore behaves considerably different from the optical activity. For the method according to the invention, a physical model is used, which describes the influence on the polarization of measurement radiation by the components of the eye, particularly by the intraocular fluid and the cornea.

16 Claims, 9 Drawing Sheets

(56) References Cited

U.S. PATENT DOCUMENTS

| | | |
|---|---|---|
| 6,704,588 B2 | 3/2004 | Ansari et al. |
| 6,885,882 B2 | 4/2005 | Cotéet et al. |
| 7,751,043 B2 | 7/2010 | Scarpaci et al. |
| 2003/0233036 A1 | 12/2003 | Ansari et al. |
| 2004/0138539 A1 | 7/2004 | Jay et al. |
| 2005/0085701 A1 | 4/2005 | Burd et al. |
| 2005/0171416 A1 | 8/2005 | Proniewicz et al. |
| 2006/0094942 A1 | 5/2006 | Winther |
| 2006/0244972 A1 | 11/2006 | Fercher |
| 2011/0105868 A1 | 5/2011 | Westphal |

FOREIGN PATENT DOCUMENTS

| | | |
|---|---|---|
| DE | 696 33 377 T2 | 9/2005 |
| DE | 10 2005 020 911 A1 | 11/2006 |
| DE | 10 2005 020 912 A1 | 11/2006 |
| DE | 10 2006 048 849 A1 | 4/2008 |
| EP | 0 160 768 A1 | 11/1985 |
| WO | WO 03/025562 A2 | 3/2003 |
| WO | WO 2004/064628 A1 | 8/2004 |
| WO | WO 2008/046464 A1 | 4/2008 |

METHOD AND DEVICE FOR MEASURING DISSOLVED SUBSTANCES IN HUMAN OR ANIMAL INTRAOCULAR FLUID

RELATED APPLICATION

This application is a continuation of U.S. application Ser. No. 12/921,747 filed Jan. 13, 2011 entitled "Method and Device for Measuring Dissolved Substances in Human or Animal Intraocular Fluid", which is a National Stage entry of PCT DE 2009/00289 filed Mar. 2, 2009 which claims priority to German Patent Application DE 102008013821.5 filed Mar. 10, 2008 all of which are hereby fully incorporated herein by reference.

FIELD OF THE INVENTION

The present invention relates to the non-invasive optical measurement of glucose and other dissolved substances in human or animal aqueous humour. A method for this as well as devices for carrying out the method are proposed.

BACKGROUND OF THE INVENTION

The glucose concentration in blood is of fundamental importance for human and animal metabolism. The following is limited to the ratios in humans but also apply in principle to numerous animals. Glucose is a central provider of energy to almost all areas of the human body. In healthy humans the glucose concentration in the blood is effectively regulated. The glucose concentration in the blood, also called blood sugar level, increases in particular after the consumption of carbohydrate-containing food. In order to counteract this, more of the hormone insulin is spilled out into the blood from the islet cells of the abdominal salivary gland. The insulin reduces the blood sugar level by transporting the glucose from the blood plasma and from the tissue liquid into the interior of the cell. If, on the other hand, the blood sugar level is too low, then principally the hormone glucagon becomes active. This regulating circle keeps the glucose concentration in the blood of healthy humans in the range of from 80-100 mg/dl (this corresponds to 4.4-6.7 mmol/l).

If there is any disruption to this regulating circle, for example due to insulin insufficiency or resistance to insulin, the glucose concentration experiences much greater fluctuations, and the symptoms of diabetes mellitus present themselves. A distinction is drawn between two diabetes types. In type 1 there is a disturbance of the islet cells in the abdominal salivary gland, with the result that in its advanced stage, no more insulin can actually be produced by the body. The islet cells are at least partly still intact in type 2, but other malfunctions, such as insulin resistance, hyperinsulinism, relative insulin insufficiency or dysendocrinisms are present. In type 1, in every case, a regular dose of externally administered insulin is required. In type 2, previously also called adult-onset diabetes, there are also various other medicaments for treatment.

According to figures from the WHO, there are approx. 8 million diabetics in Germany alone, with an estimated worldwide figure of 300 million by the year 2025. Above all in industrialized nations, the relative proportion of diabetics in the population has also been increasing clearly for years.

If diabetes is not treated, in the event of chronic hyperglycaemia a patient can suffer massive damage to eyes, organs and limbs. While hypoglycaemia can easily be recognized by patients themselves who know about their illness thanks to various symptoms and compensated for by taking dextrose, the position is different with hyperglycaemia. Too high a blood sugar level is barely detectable by those affected.

In both diabetes types the blood sugar level must therefore be measured at regular intervals in order to be able to ascertain the optimum dose of insulin or other medicaments. In extreme cases the glucose concentration in the blood can increase to up to 1000 mg/dl, which corresponds to approximately ten times the normal concentration. Relatively frequently, concentrations of up to 300 mg/dl occur, in particular after consuming too many carbohydrates. The absolute standard for measuring the blood sugar level by the doctor or the patient himself is currently the use of so-called blood sugar measurement strips. Their use requires blood to be taken from the diabetic. If no blood sample is already available, the diabetic generally pricks a fingertip with a special needle in order to obtain a drop of blood. The drop of blood is placed on the blood sugar measurement strips. An enzymatic reaction takes place, after which the glucose concentration can be determined via an electrical measurement. The glucose concentration is required to be ascertained with an error of at most 15%. Depending on the phase of the illness and markedness the measurement must be repeated up to seven times a day.

The disadvantages of this invasive measurement method are obvious: 1. Pricking the fingertip is extremely painful. 2. Skin impurities can lead to measurement errors. 3. There is an increased risk of infection due to the frequent damaging of the skin. Additionally, the blood sugar measurement strips have limited storability. The high number of non-reusable blood sugar measurement strips results in enormous costs for health insurers and patients.

It is known that the glucose concentration in the aqueous humour accounts for approximately 70% of the glucose concentration in the blood, wherein the temporal concentration pattern in the blood is some minutes ahead of the aqueous humour. The glucose in the aqueous humour serves above all to supply energy to the cornea and the lens of the eye, as these two constituents of the eye must not contain any blood vessels, for optical reasons. In order to avoid the mentioned disadvantages of the blood sugar measurement strips it can be attempted to measure the glucose concentration in the blood indirectly via the glucose concentration in the aqueous humour. The aqueous humour is a clear liquid in the anterior and posterior chambers of the eye. Only the anterior chamber, which is located between cornea and lens of the eye, is sufficiently accessible. Because of the blood-aqueous humour barrier, the aqueous humour contains a type of ultrafiltrate of the blood. In other words, nearly all cell constituents and proteins are filtered out with the result that only water, dissolved salts and small dissolved molecules still enter the aqueous humour. The dissolved substances in the aqueous humour include i.a. NaCl, glucose, lactate, ascorbic acid, amino acids and urea.

In principle, essentially the following optical methods are conceivable for measuring the glucose concentration in the aqueous humour: interferometry, confocal measurements, polarimetry, reflectometry, measurement of Raman scattering and absorption measurements in the infrared range. There are already publications relating to each of the methods. Thus far, however, a sufficient precision and reliability when determining the glucose in the aqueous humour has yet to be achieved with any of the methods. As the glucose generally dominates the optical activity in the aqueous humour, polarimetry is a priori a relatively specific method, i.e. there is a good correlation between optical activity and glucose concentration. It is this which basically distinguishes polarimetry from most other optical methods. Interferometric methods react for example very sensitively to the relatively strongly fluctuating salt content of the aqueous humour. As salts do not display any optical activity at all, polarimetry is completely insensitive to fluctuations in salt concentration. The present invention can be considered to use polarimetry, therefore the further description of the state of the art will concentrate on this method.

An array is described in U.S. Pat. No. 3,963,019A1 in which a light beam strikes the iris of the eye and the light reflected or scattered by the iris is detected with an optical analyzer. In one embodiment the light beam is polarized, and a second polarizer is located in front of the optical analyzer. The measurement array is calibrated using a known glucose concentration. It is proposed to measure the blood sugar level with this array. For the following reasons it can, however, be assumed that this is not possible with the described array. With an assumed glucose concentration of 100 mg/dl, the rotation of the polarization plane through the glucose is only approximately 0.005 degrees. Because of the medically necessary relative precision of 15% when determining the concentration, a rotation of 0.00075 degrees must be triggered. In order to be able to measure such small changes there must be a relative intensity resolution of better than 1E-4. However, light sources generally have temporal drifts or fluctuations in the radiated intensity which lie at least in the permil range, but frequently even in the percent range. This applies both to incandescent lamps and arc lamps and to light-emitting diodes and lasers. Moreover, the eye carries out saccades and microsaccades, i.e., involuntary movements. The region of the iris which the light beam strikes thereby fluctuates. As the iris has reflection and scatter characteristics which display pronounced spatial variations, the result is an additional considerable fluctuation in intensity at the optical analyzer. The expected fluctuations in intensity due to the light source and the saccades prevent the much smaller variations in intensity due to the polarization rotation from being able to be measured with the described array.

A device is described in document DE4243142A1 which is very similar to that in U.S. Pat. No. 3,963,019A1, but also has a Faraday modulator with which the input polarization can be periodically varied. In combination with a lock-in amplifier, the Faraday modulator is intended to improve detection. However, left completely out of account is the fact that the measurement radiation must pierce the extremely birefringent cornea twice. It can be assumed that the birefringence of the cornea influences the polarization of the measurement-radiation light at least a thousand times more strongly than the glucose in the aqueous humour. The degree of the corneal birefringence depends greatly on the polarization direction in which the cornea is irradiated. By using the Faraday modulator, mainly a varying birefringence is induced which is much greater than the change in polarization of the glucose. The same problems as have already been named with regard to U.S. Pat. No. 3,963,019A1 also occur.

U.S. Pat. No. 6,704,588B2 proposes a method in which the lens of the eye is irradiated exactly at Brewster's angle, in order to create pure s-polarization when the radiation is reflected by the lens of the eye. However, it must be assumed that this approach is insufficient to compensate for the influence of the saccades and microsaccades. The problem is that the eye movements cause not only variations in the birefringence but also variations in the angle of incidence at the lens of the eye. Even if the angle variations are only fractions of a degree, the changes in polarization due to the fluctuating angle of incidence and the fluctuating birefringence are much greater than the polarization influence due to the glucose in the aqueous humour. As these effects cannot be separated on detection side, it appears unrealistic that physiological glucose concentrations in the aqueous humour can be measured with the method.

A device is described in DE102005020912A1 in which a polarization-rotating element, such as e.g. a lambda/2 plate, is used. The aim is to poll the polarization-changing action of the whole eye for as many different input polarizations as possible of the measurement radiation. Here, too, the problem is that on detection side it can no longer be distinguished whether or to what extent a certain change in polarization has been caused by the glucose, the birefringence of the cornea or the reflection at the lens of the eye.

DE102005020911A1 proposes a measurement concept in which, using Faraday modulators, at least two different polarizations of the input radiation are produced, in order firstly to produce a defined polarization state at the lens of the eye. Starting from this initial condition at the lens of the eye it is expected that subsequently only the polarization rotation of the glucose and the birefringence of the second corneal passage still change the polarization. Because the glucose causes only a rotation of the polarization plane, but the corneal passage a phase shift between s- and p polarization, there is the chance that the influence of the glucose can be measured via the rotation of the resulting polarization ellipse after the measurement radiation leaves the eye. However, the device is very costly and requires the use of Faraday modulators which are expensive and difficult to operate.

SUMMARY OF THE INVENTION

The object of the present invention is to avoid the described problems of the state of the art and to provide methods as well as devices for carrying out the methods with which the concentration of glucose and other optically active substances in the aqueous humour can be measured non-invasively, in order to deduce therefrom the blood sugar level, the blood lactate level or other physiological parameters. The main problem with a polarimetric approach is distinguishing the polarization rotation of the glucose or the other optically active substances in the aqueous humour from the birefringence of the cornea. In addition to glucose, essentially the following substances are also optically active in the aqueous humour: ascorbic acid, lactate and amino acids. The invention is therefore also intended to make it possible to measure the concentrations of these substances. A supplementary aim of the invention is to produce a device suitable for measuring blood sugar which manages without cost-intensive Faraday modulators.

DETAILED DESCRIPTION OF THE DRAWINGS

The invention solves the formulated problem by a polarimetric method in which the clearly different wavelength dependencies of the optical activities and the birefringence of the cornea are logically exploited. To illustrate the method it is necessary firstly to describe the device according to the invention for carrying out the method.

a) Device According to the Invention

Figure 1:
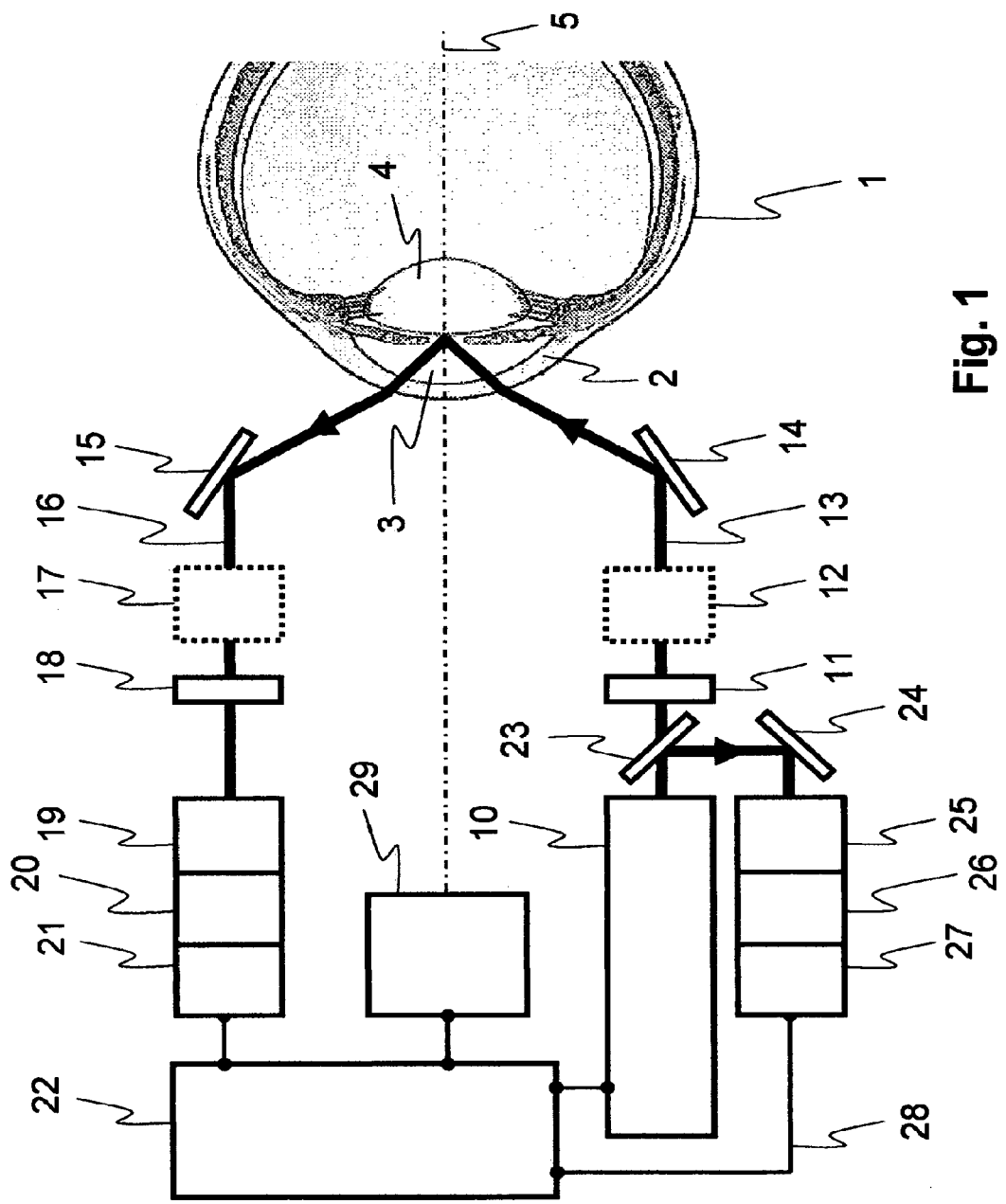
FIG. 1 depicts a schematic overview of the device according to the invention.

FIG. 1 shows a schematic overview of the device according to the invention. The polarimetric measurement is carried out on an eye 1 which has the cornea 2, the anterior aqueous humour 3 and the lens of the eye 4. The line connecting the centre of the iris and the centre of the fovea centralis (region of the sharpest vision) is here called optical axis 5. The device contains a radiation source 10 which can emit collimated radiation at least in the spectral range of 440 nm to 700 nm, but preferably in an even broader spectral range of from 330 to 1050 nm. The radiation given off by the radiation source 10 is polarized with a polarizer 11. In one embodiment, this is preferably a linear polarizer but a circular polarizer can also be used for example. The polarized radiation 13 is directed onto the lens of the eye at an angle of incidence of for example more than 20 vis-à-vis the optical axis 5. However, with smaller angles of incidence a measurement is also possible. In this case it is to be taken into account that a not insignificant refraction of the collimated beam generally takes place at the air-cornea interface. As the accessibility of the eyes is impaired by the eyelids, eyelashes and the nose, it is geometrically advantageous to apply the measurement radiation to the eye via a mirror 14. The mirror 14 can be designed as a metallic surface but also as a prism and should influence the previously prepared polarization as little as possible. Supplementarily, means can be provided to move eyelids and eyelashes aside for good optical accessibility. The measurement radiation 13 pierces firstly the cornea 2 and then the aqueous humour 3, before being reflected at the lens of the eye 4. After reflection the measurement radiation penetrates the aqueous humour and the cornea a second time. After leaving the eye the measurement radiation 16 is directed onto a further polarizer 18. Here, too, it is advantageous, for reasons of accessibility, to use a further deflection mirror 15. After passing through the polarizer 18, which can be a linear polarizer, circular polarizer or elliptical polarizer, the measurement radiation is passed to a spectrometric array 19-21.

The components 23-27, with which a spectrally resolved reference measurement can be carried out simultaneously with the actual measurement, are particularly advantageous for the measurement precision and reliability of the device. For this, some of the measurement radiation is branched off with a beam splitter 23 for the reference measurement. The branching off takes place in FIG. 1 directly following radiation source 10. In principle, however, any other position in front of the polarizer 18 is also suitable for splitting off the reference radiation. The reference radiation is passed to a further spectrometric array 25-27 by a deflection mirror 24.

Additionally, the measurement device according to the invention contains an alignment device 29 with the help of which the optical axis of the eye is aligned vis-à-vis the measurement device. A luminous display, for example an OLED or LCD display, with which a spatially and temporally variable fixing light can be projected into the eye, is an essential constituent of the alignment device 29. All electronically drivable or readable components are connected to the control unit 22, shown in the example by the data line 28. Additionally, the alignment device 29 can be supplemented by a camera to observe the iris in order to achieve an even better alignment of the eye vis-à-vis the measurement device. Optionally the measurement device also contains two optical phase shifters 12 and 17 with which the polarization state of the measurement radiation can be changed in targeted manner between s- and p polarized radiation with regard to the phase. These phase shifters serve to compensate for the individual birefringence properties of the cornea. The phase shifters can for example be designed as variable Babinet or Soleil compensators. If the ideal individual phase shift is known, they can also be realized by phase plates with fixed phase shift. The precise purpose of the phase shifter is explained further below.

Figure 2:
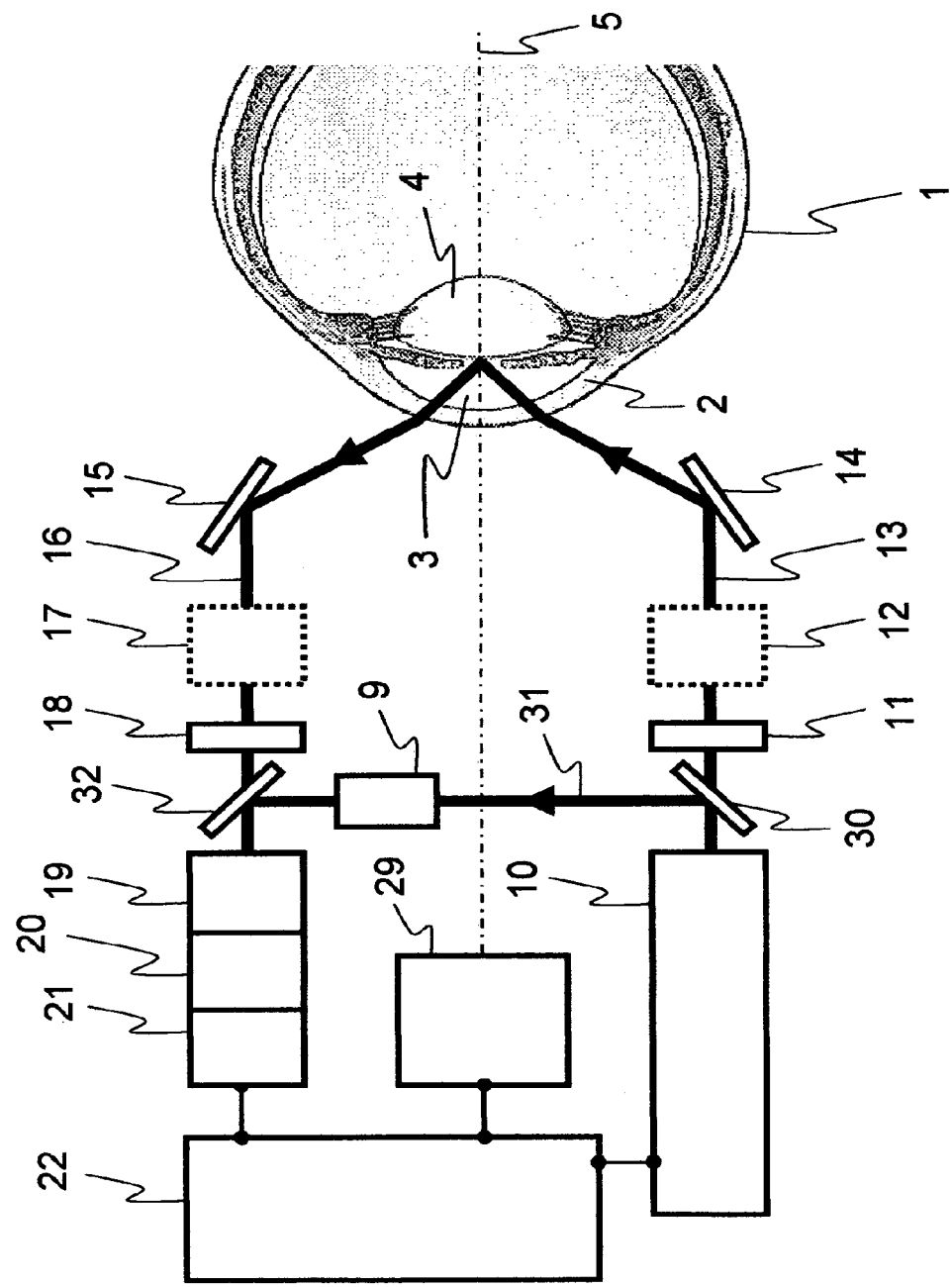
FIG. 2 depicts another embodiment the measurement device according to the invention in which a spectrometric array is also used for simultaneous measurement of reference radiation.

A further design variant of the measurement device according to the invention is shown in FIG. 2 in which the spectrometric array 19-21 is also used for simultaneous measurement of reference radiation in order to simplify the device and save on production costs. Here the reference radiation 31 is split off with the beam splitter 30. The reference radiation 31 is passed to the spectrometric array 19-21 via an optical shifter 9 and the beam splitter 32. The shifter 9, which for example can consist of two deflection mirrors, an equivalent prism array or a flexible optical fibre, ensures that the reference radiation strikes a different region of the spectrometric array 19-21 than the actual measurement radiation, with the result that a simultaneous measurement of reference radiation and measurement radiation is possible. In particular the optical detector 21 can be a two-dimensional array of detector elements, i.e. a digital camera. After the spectral splitting-up by the spectrally acting element 19 and the lens 20 the measurement radiation strikes one part of the detector elements, while the reference radiation strikes another part of the detector elements because of the beam shift. The spectral resolution for the measurement radiation and the reference radiation should be as equal as possible, because spectrally corresponding reference values of the reference radiation should be available for all spectral portions of the measurement radiation.

Figure 3:
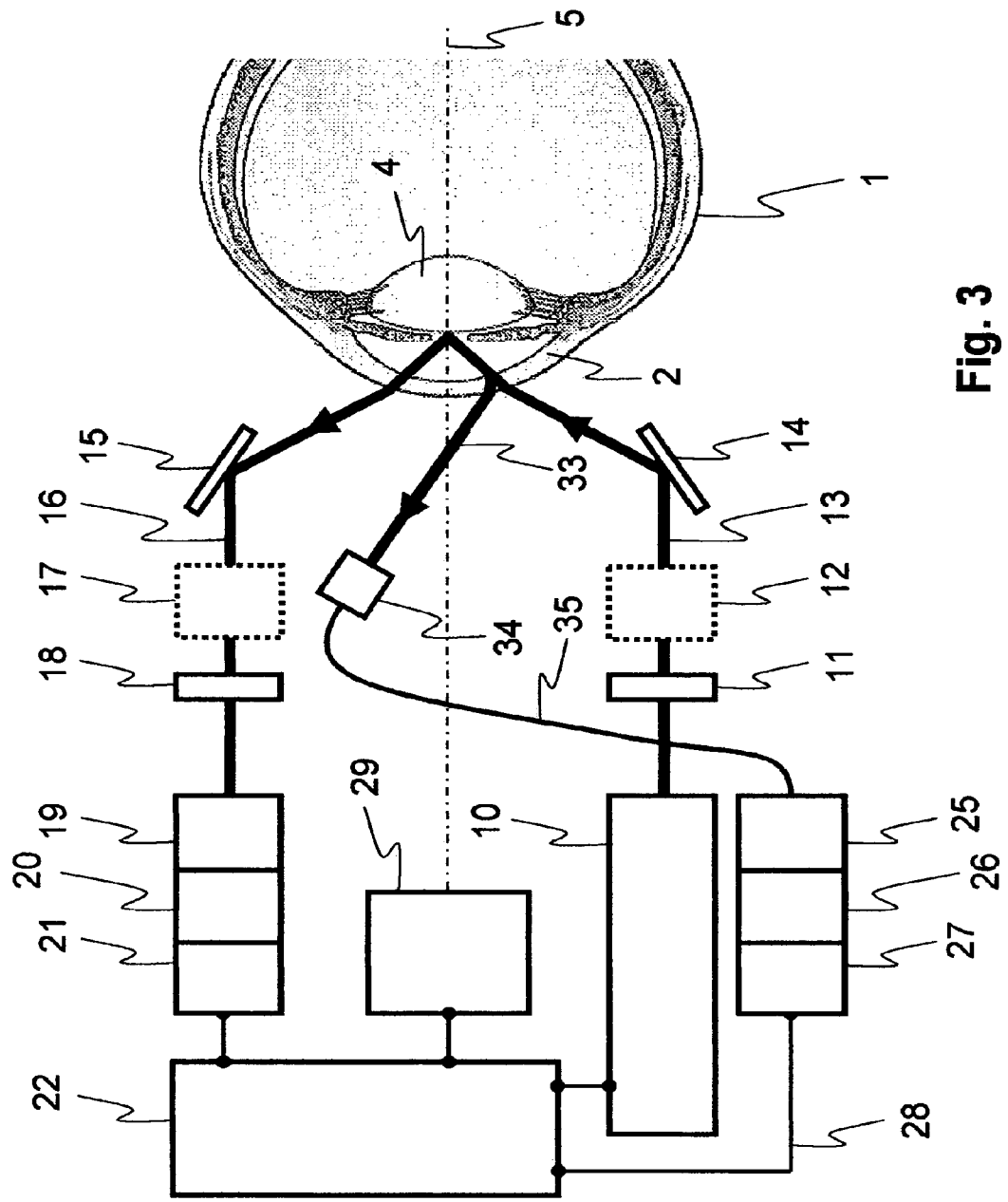
FIG. 3 depicts another embodiment the measurement device according to the invention in which in which the splitting off of the reference radiation takes place at the cornea-aqueous humour interface.

FIG. 3 shows a third design variant of the measurement device according to the invention, in which the splitting off of the reference radiation takes place, not directly following the radiation source 10 but firstly at the cornea-aqueous humour interface. Spectral influences of the components 11-14 lying in front can also thereby be recorded. Here, the reference radiation 33 is passed via the lens 34 to the optical fibre 35 and then the spectrometric array 25-27. Instead, naturally, as in FIG. 2, the spectrometric array 19-21 can also be used for the measurement of reference radiation. The reference radiation can also be split off elsewhere, e.g. upon entry into the eye at the cornea-air interface or after leaving the eye behind the components 15 or 17. In order to be able to record spectral changes to the measurement radiation in front of the polarizer 18 even more precisely it may also be useful to split off the reference radiation at several different points and simultaneously carry out spectral measurements.

All variants of the spectrally resolved measurement of reference radiation serve to record very small spectral fluctuations in measurement radiation following the polarizer 18 which are not attributable to polarization effects of the eye, with a relative intensity resolution of better than 10E-4. This is necessary in order to achieve the great accuracy which the method according to the invention for determining the glucose concentration in the aqueous humour requires. Very small fluctuations in the spectral portions of the radiation source 10 or of the spectral transmission or reflection properties of all components of the measurement device or also the eye components can distort the measurement result. The largest source of error is the radiation source 10, because in principle with all known broadband radiation sources wavedependent fluctuations of the radiated power must be calculated in the percent range. In order to achieve the required relative intensity resolution of better than 10E-4, all detector elements of the optical detector 21 or 27 have a dynamic resolution of at least 10 bits, in another embodiment 11 to 18 bits, and in another embodiment 14 to 16 bits. In the case of less than 14 bits dynamic resolution, which may be advisable for reasons of low production costs, the actually too small dynamic resolution can for the most part be compensated for by averaging over many redundantly measuring detector elements.

Figure 4:
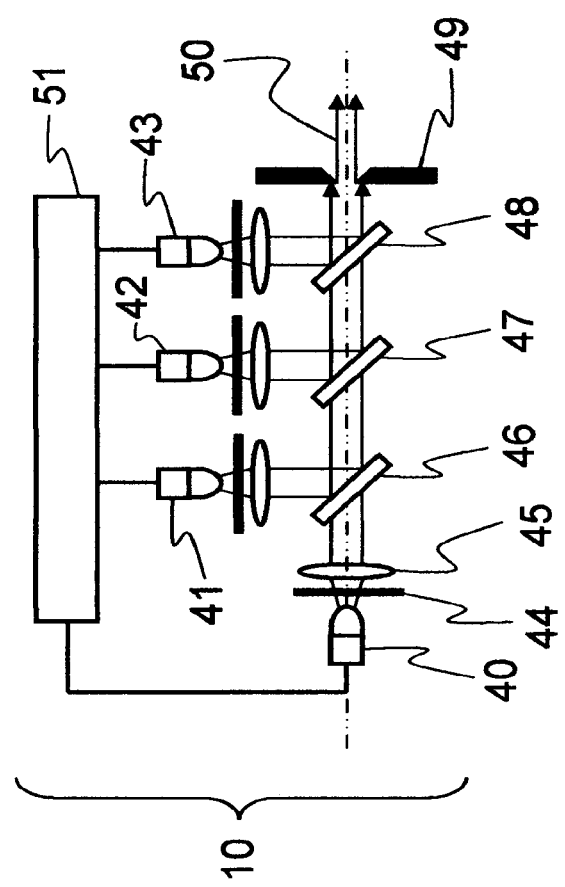
FIG. 4 depicts an embodiment of a radiation source according to the invention.
Figure 5:
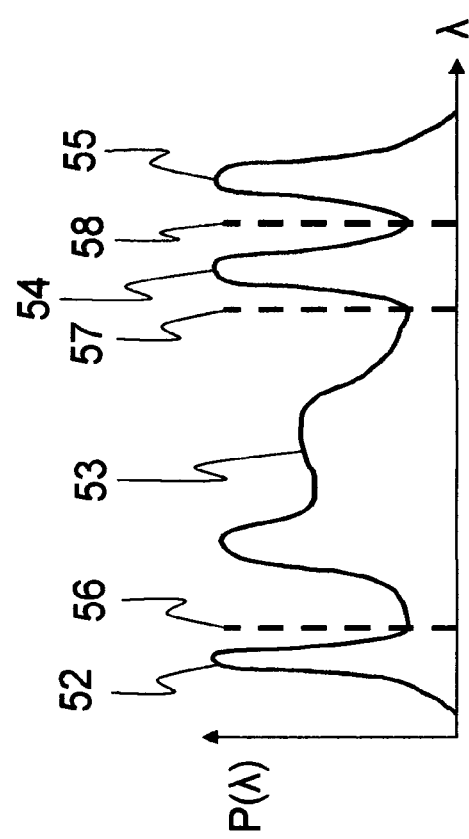
FIG. 5 depicts an example spectrum suitable for the method according to the invention.

An example embodiment of the radiation source 10 is shown in FIG. 4. The radiation is produced by the individual radiation sources 40-43 which have different centroid wavelengths. The individual radiation sources 40-43 are preferably LEDs, i.e. light-emitting diodes. FIG. 5 shows a whole spectrum suitable for the method according to the invention which provides the radiation source 10. It is composed of the four individual spectra 52-55, wherein spectrum 52 is allocated to LED 43, spectrum 53 to LED 42, spectrum 54 to LED 41 and spectrum 55 to LED 40. LED 43 has its centroid wavelength preferably in the range of from 360 nm to 440 nm, LED 42 in the range of from 450 nm to 610 nm, LED 41 in the range of from 620 to 690 nm and LED 40 in the range of from 700 to 900 nm. LED 42 may be a so-called white-light LED, the spectrum of which is composed of blue primary light and yellow fluorescence light from a luminescent material. Alternatively LED 42 can also be a green LED with as broad as possible a spectrum. In order to configure the spectral minima less pronouncedly in addition to the white-light LED the three other LEDs can also each be provided with a different luminescent material. In the embodiment example in FIG. 4 the LED radiation is initially homogenized with diffusers 44 (for example holographic diffusers) such that the radiation can subsequently be well collimated with the focussing lenses 45. The spectral bunching into a joint beam path takes place with the dichroitic beam mergers 46-48 which act as spectral long passes in transmission. The spectral edges of the dichroites are shown in FIG. 5 by the lines 56-58. The beam cross-section is formed by a preferably rectangular diaphragm 49 before the resulting radiation 50 leaves the radiation source 10. The LEDs are powered by a control unit 51. The thus-designed radiation source 10 has the particular advantage that, with the help of the control unit 51, any desired combinations of the LED can be switched on and off. Thus the whole spectrum can vary in targeted manner, which is useful for calibration purposes. Similarly, a different number of LEDs can also be used. In principle it is sufficient, however, to also use a single white-light LED, or an UV LED, to which several luminescent materials are applied, in order to carry out the method according to the invention.

The LEDs can also be replaced by superluminescence diodes or laser diodes which, because of the spatial coherence, have the advantage of better collimatibility, but also lead to less favourable spectral properties. A further alternative is the use of a very broadband radiation source, such as e.g. halogen lamps, arc lamps or continuum lasers. A broadband continuum laser has the advantage that, in spite of the broad spectrum it is well collimatible, i.e., without great losses of output. A disadvantage is, however, the complex and thus expensive structure of a continuum laser.

Figure 6:
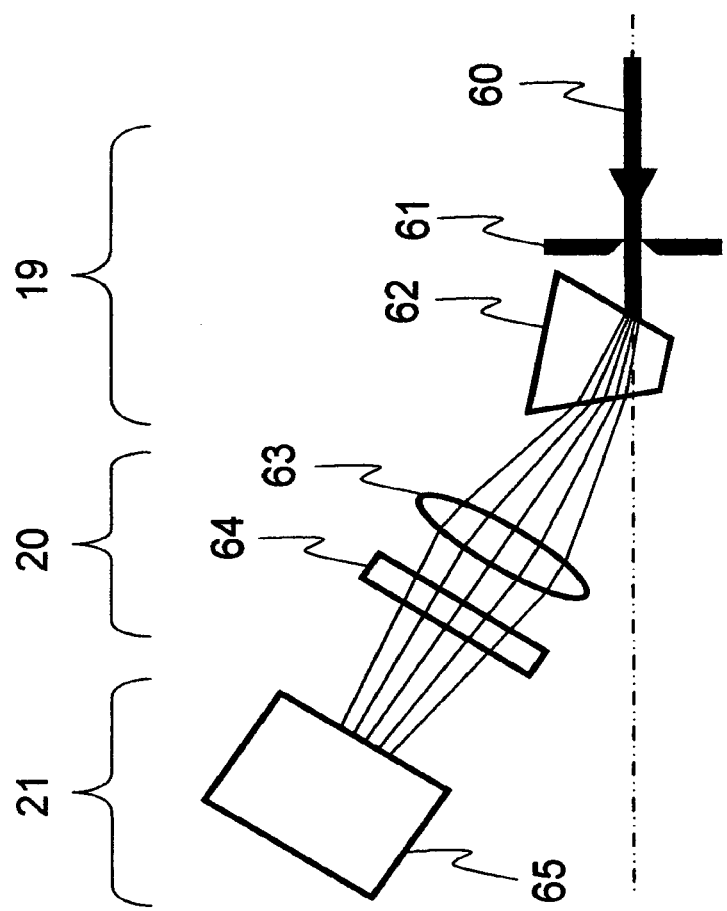
FIG. 6 depicts an example embodiment example of a spectrometric array according to the invention.

FIG. 6 shows an embodiment example for the spectrometric array 19-21 and 25-27 respectively. The measurement radiation or reference radiation 60 initially retains a clean rectangular profile with the help of the diaphragm 61. The radiation 60 is spectrally decomposed with a strongly dispersive prism 62 such that different wavelengths lead to different deflection angles. To increase the deflection angles, several prisms can also be used one behind the other. Alternatively the spectral decomposition can also take place with gratings or other spectrally acting elements. The spectrally decomposed radiation is mapped on a two-dimensionally position-resolving intensity detector, preferably a CCD or CMOS camera, with a first cylindrical lens 63. It is not necessary to achieve a particularly high spectral resolution. What is important is that the entire width of the intensity detector 65, i.e., a high number of individual detectors (pixels), is used. A suitable number is approximately 100 to 1000 pixel columns. It is advantageous with the method according to the invention to have available a large number of intensity measurement values. A second cylindrical lens 64, whose axis of symmetry runs perpendicular to that of the cylindrical lens 63, compresses the measurement radiation onto a strip in the non-spectrally split direction. The height of the strip on the intensity detector 65 can be chosen via the distance between cylindrical lens 64 and intensity detector 65. The height is chosen such that preferably 50 to 500 pixel lines are irradiated. Each of these pixel lines delivers theoretically redundant spectral data which differ essentially only in their noise. The accuracy of the method according to the invention can be clearly improved because of the high number of redundant spectral data. Alternatively the high number of redundant intensity values can also be achieved using a camera with only a few lines or a single-line camera if the image read-out rate is correspondingly higher.

The optical detector 21 or 27 can also consist of a line-type array of preferably at least eight photodiodes. Thus, generally, a much lower spectral resolution can be achieved than with a CCD or CMOS camera. However, discrete photodiodes have the advantage that they can be electronically read very quickly and with high intensity dynamics. Furthermore, photodiodes have the advantage that they are much more cost-effective, even in double digit number, than a camera with high intensity dynamics, and thereby make possible the production of the device according to the invention at much lower costs than when using cameras.

Figure 7:
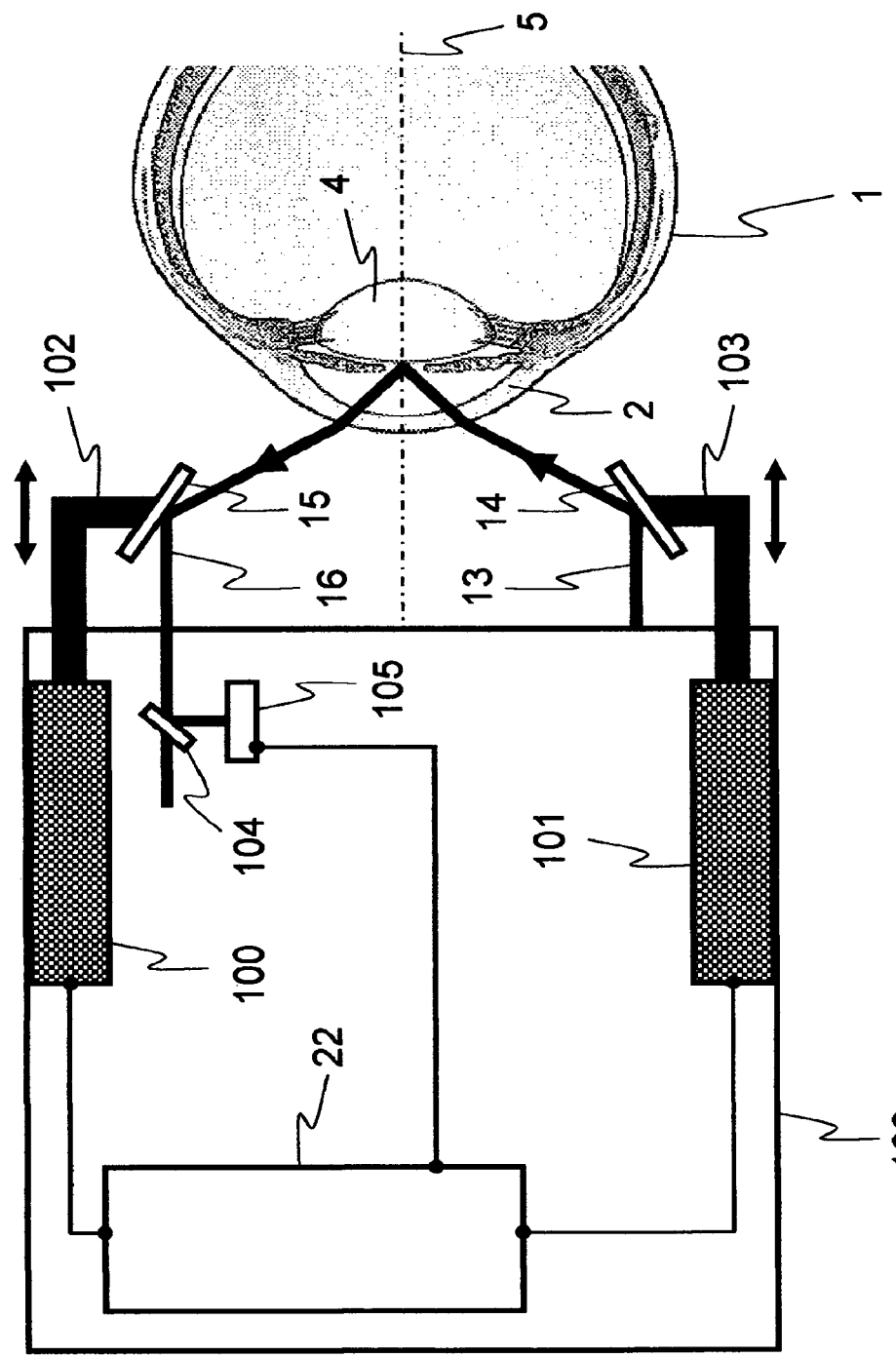
FIG. 7 depicts how the measurement device according to the invention can advantageously be aligned electromechanically vis-à-vis the eye.

In FIG. 7 it is shown how the measurement device according to the invention can advantageously be aligned electromechanically vis-à-vis the eye. Firstly the components 100-103 shown in FIG. 7 serve to optimize the site of the reflection of the measurement radiation at the lens of the eye 4. The optimum site of reflection is located in the centre of the front of the lens of the eye. This site essentially coincides with the centre of the iris. According to the invention, the optimum setting of the place of reflection takes place by linear shift of the deflection mirrors 14 and 15. The shift of the deflection mirrors 14 and 15 takes place in the direction of the beam paths 13 and 16 respectively, whereby it is guaranteed that the beam paths 13 and 16 do not experience changes of angle. Additionally it is thereby achieved that the angle of incidence at the lens of the eye remains largely the same. The shift of the deflection mirrors 14 and 15 takes place through the actuators 100 and 101 which are connected to the deflection mirrors 14 and 15 via the servoelements 102 and 103. The actuators 100 and 101 can for example be realized with piezo drives, spindle drives, stepping motors or galvanic drives. The actuators 100 and 101 are controlled by the control unit 22. The positioning is controlled e.g. by splitting off a part of the measurement radiation via the beam splitter 104 and directing it onto the optical detector 105. The detector 105 preferably consists of a small camera matrix with which the centroid and the intensity of the split-off beam can be determined. Alternatively, instead of the camera matrix also a position-sensitive detector (PSD) or, in the simplest case of the pure intensity measurement, a photodiode can be used. The detector 105 is also connected to the control unit 22. The entire measuring array, thus also the components shown in FIGS. 1-3, are housed in an optically and electromagnetically screened housing 106.

The deflection mirrors 14 and 15 can also be designed such that they can be tilted by hand or by motor. In cooperation with actuators 100 and 101 the angle of incidence on the cornea can then be varied in targeted manner in order to minimize the corneal birefringence.

Figure 8:
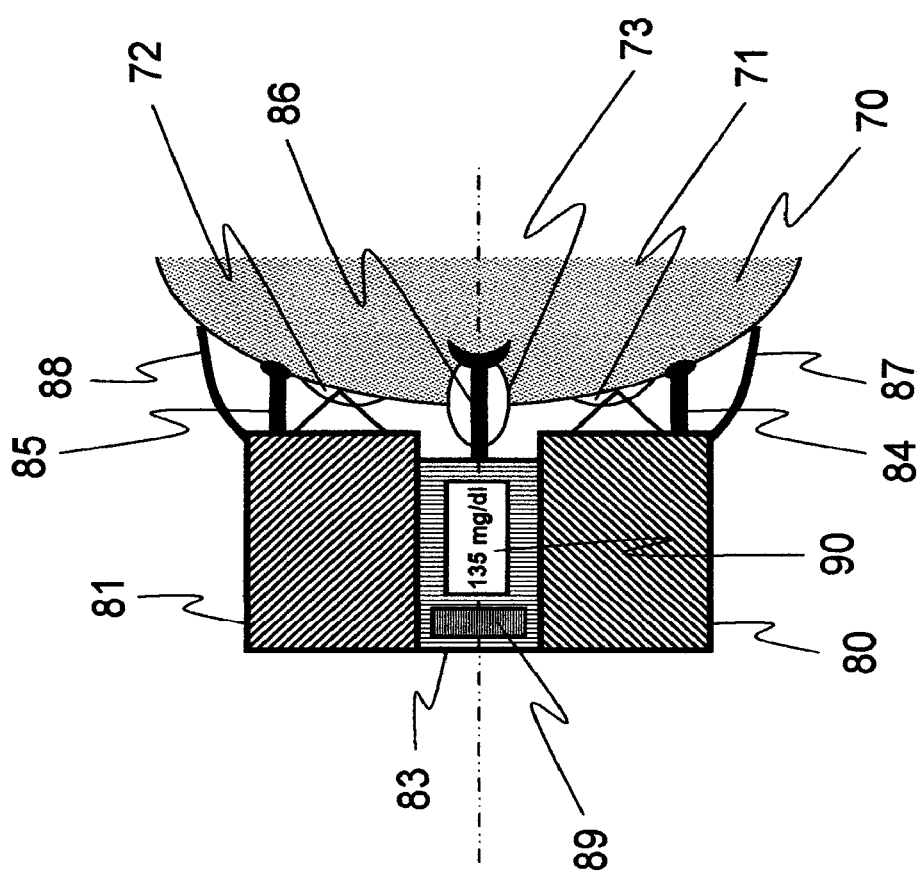
FIG. 8 shows an embodiment variant of the invention in which two of the individual measurement devices from FIG. 1-3 or 7 are used on both eyes simultaneously, quasi-simultaneously or alternately.

FIG. 8 shows an embodiment variant of the invention in which two of the individual measurement devices from FIG. 1-3 or 7 are used on both eyes simultaneously, quasi-simultaneously or alternately. The accuracy of the measurement values can thereby be increased and potential measurement problems due to injury or disease in one of the two eyes can be circumvented by measuring the other eye in each case. A human head 70 with eyes 71 and 72 as well as nose 73 is shown schematically from above in FIG. 8. The embodiment variant contains the two individual measurement devices 81 and 82, a connecting part 83, the spacers 84-86 and the optical shieldings 87 and 88. The connecting part 83 can have an input area 89 for manual operation and a display to show the measurement result and operating parameters. The spacers 84 to 86 here form a three-point positioning of the whole measurement device on the head 70. The spacers are matched individually to the shape of the head in order to achieve a good prepositioning of the measurement device. The spacers 84 and 85 are preferably attached to the forehead while the spacer 86 is preferably attached to the bridge of the nose. The optical shieldings 87 and 88 are designed preferably flexible, for example of blackened rubber or woven fabric. However, they can also consist of an individually matched plastic dish.

The embodiment variant in FIG. 8 can also, for reasons of cost, contain only one individual measurement device 81 or 82, but all the other components. In this case it is preferred that the embodiment variant is designed such that by rotating the entire measurement device by 180° or shifting the one individual measurement device measurement is possible at both the right and the left eye.

b) Method According to the Invention

The method according to the invention principally exploits the fact that the wavelength dependency of the optical activity is fundamentally different from that of the corneal birefringence. The optical activity of substances dissolved in the aqueous humour, such as glucose, lactate, ascorbic acid or amino acids is scaled in a first approximation with the reciprocal of the squared wavelength. On closer inspection, higher orders are to be taken into account, and effectively an exponent deviating from value 2 can occur. In the case of glucose the exponent may be called $2+x_G$, wherein the value $x_G$ is approximately 0.2. Correspondingly the exponents in the case of lactate are $2+x_{Lac}$, in the case of ascorbic acid $2+x_{Asc}$ and in the case of amino acids $2+x_{Am}$. Further optically active substances can likewise be taken into account but are largely negligible. A necessary constituent of the invention is to know with great accuracy the values $x_G$, $x_{Lac}$, $x_{Asc}$ and $x_{Am}$. As the values are only insufficiently known from the literature, to carry out the method according to the invention they are to be metrologically determined on a one-off basis. With commercially available optical components this is not a problem for a person skilled in the art.

The corneal birefringence is scaled, on the other hand, with the reciprocal of the wavelength and thus behaves clearly differently from the optical activity. For the method according to the invention a physical model is produced which describes the influencing of the polarization of measurement radiation by the components of the eye, in particular by the aqueous humour and the cornea. The physical model can be an approximation but must take sufficiently precise account of the wavelength dependencies. By way of example the following equation (1) is cited as physical model:

$$I(\lambda) := I_0(\lambda) \cdot \cos\left(\alpha_{Pol}(\lambda) + const_G \cdot \frac{conc_G}{\lambda^{2+x_G}} + \frac{1}{2} \cdot \frac{\mathrm{atan}(const_{DB} \cdot \cos(\theta_m + \Delta\theta))}{\lambda} - \frac{1}{2} \cdot \frac{\mathrm{atan}(const_{DB} \cdot \cos(\theta_m))}{\lambda}\right)^2$$

Equation (1) describes the intensity behind the polarizer 18 of the device according to the invention in relation to the wavelength $\lambda$. It is assumed that the measurement radiation displays an elliptical polarization in front of the polarizer 18. $I_0(\lambda)$ represents the spectral intensity distribution in front of the polarizer 18. The polarizer 18 is here assumed to be a linear polarizer, the polarization direction of which is set such that at a specific wavelength $\lambda_0$ the angle $\alpha_{Pol}(\lambda_0)$ is between the polarization direction and the main axis of the polarization ellipse. The wavelength $\lambda_0$ is preferably a wavelength which can be well set with the device according to the invention, thus for example one of the LED centroid wavelengths. The radiation source 10 according to FIG. 4 proves advantageous here because the spectrum of an individual LED can thus be made available in targeted manner. $\alpha_{Pol}(\lambda_0)$ is preferably set to 45° as at this angle the change in intensity is particularly great in relation to a change in position of the main axis of the polarization ellipse. As the optical activity increases greatly at small wavelengths, an LED centroid wavelength of preferably <500 nm is used for $\lambda_0$ in order to achieve a large measurement effect.

The second term in the argument of the $\cos^2$ function represents the optical activity of the glucose in the aqueous humour. The factor $const_G$ contains the specific rotation of glucose and the section of the aqueous humour pierced by the measurement radiation. As this section varies individually it must be measured on a one-off basis. Commercially available appliances—mostly based on optical coherence tomography (OCT)—with which the anterior chamber of the eye can be geometrically measured, are available to an ophthalmologist. The section of the aqueous humour pierced by the measurement radiation can be ascertained if the angle of incidence at the lens of the eye is known. The supplementing of the device according to the invention by a miniaturized OCT appliance for geometric measurement of the anterior chamber of the eye may be advisable in order, above all with children, to be able to regularly check or adapt the geometric conditions in equation (1). For reasons of clarity only the optical activity of the glucose is shown in equation (1). The optical activity of further substances can be taken into account by adding corresponding terms in the argument of the $\cos^2$ function.

The third term in the argument of the $\cos^2$ function describes the rotation of the main axis of the polarization ellipse due to the corneal birefringence. The value $\theta_m$ represents the average phase shift caused by the birefringence, to which is added a birefringence fluctuation $\Delta\theta$ due to the saccades or microsaccades. It is assumed that $\Delta\theta_m$ is $<<\theta_m$, as the eyes carry out only very small angle movements. The factor $const_{DB}$ is, just like $\theta_m$, an individually varying parameter. The influence of $\theta_m$ on the position of the main axis of the polarization ellipse is eliminated according to the invention by individually adapting the polarizer 18 as described in more detail above. In equation (1) this adaptation is taken into account by the addition of a fourth term which describes the birefringence without adding $\Delta\theta$. The two last terms therefore cancel each other out for $\Delta\theta=0$.

With each spectral individual measurement with the device according to the invention it must be assumed that $\Delta\theta$ has changed compared with the previous measurements because of the saccades or microsaccades. The phase shift $\Delta\theta$ generally causes greater rotations of the polarization ellipse than the optically active substances in the aqueous humour. Therefore, a greater number of spectral individual measurements is required in order to measure the concentration of the optically active substances. The number of spectral individual measurements should be at least 100, preferably more than 1000. In order to limit the total measurement time to approximately one second, the spectral measurement array 19-21 and 25-27 respectively is designed such that an individual measurement preferably lasts less than 10 ms.

Calibration Method:

Calibration of the method according to the invention takes place by measurement at known concentrations of the optically active substances. The glucose concentration $conc_G$ in the aqueous humour can be ascertained via one or more invasive measurement[s] of the blood sugar level because the glucose concentration in the aqueous humour corresponds to approximately 70% of the blood sugar concentration. The spectral intensity distribution $I_{meas}(\lambda)$ is measured by the measurement device according to the invention. By means of equation (1) a corresponding theoretical value $I_{sim}(\lambda)$ is simulated, wherein the parameters $\theta_m$ and $const_{DB}$ are systematically varied in the physiologically useful range. The sum of the squared differences of $I_{meas}(\lambda)$ and $I_{sim}(\lambda)$ are calculated for each combination of parameters $\theta_m$ and $const_{DB}$, wherein averaging is carried out over numerous spectral individual measurements as well as over numerous discrete values. That combination of parameters $\theta_m$ and $const_{DB}$ at which the smallest sum of the squared differences of $I_{meas}(\lambda)$ and $I_{sim}(\lambda)$ occurs is selected. Inasmuch as the sums fluctuate greatly in the case of small changes in parameters, a two-dimensional fit to the sum values is created. The combination of parameters to be chosen then results from the minimum of the fit surface. The parameter $\theta_m$ can alternatively also be ascertained at corresponding cost via a transmission-ellipsometric measurement at the eye. For this it is helpful to produce a defined polarization state at the lens of the eye, which can be achieved by irradiation at Brewster's angle onto the lens of the eye. In this case the radiation reflected by the lens of the eye is s-polarized, with the result that, after the measurement radiation has left the cornea, $\theta_m$ is directly correlated with the angle between the main axis of the polarization ellipse and the perpendicular on the incidence plane.

Figure 9:
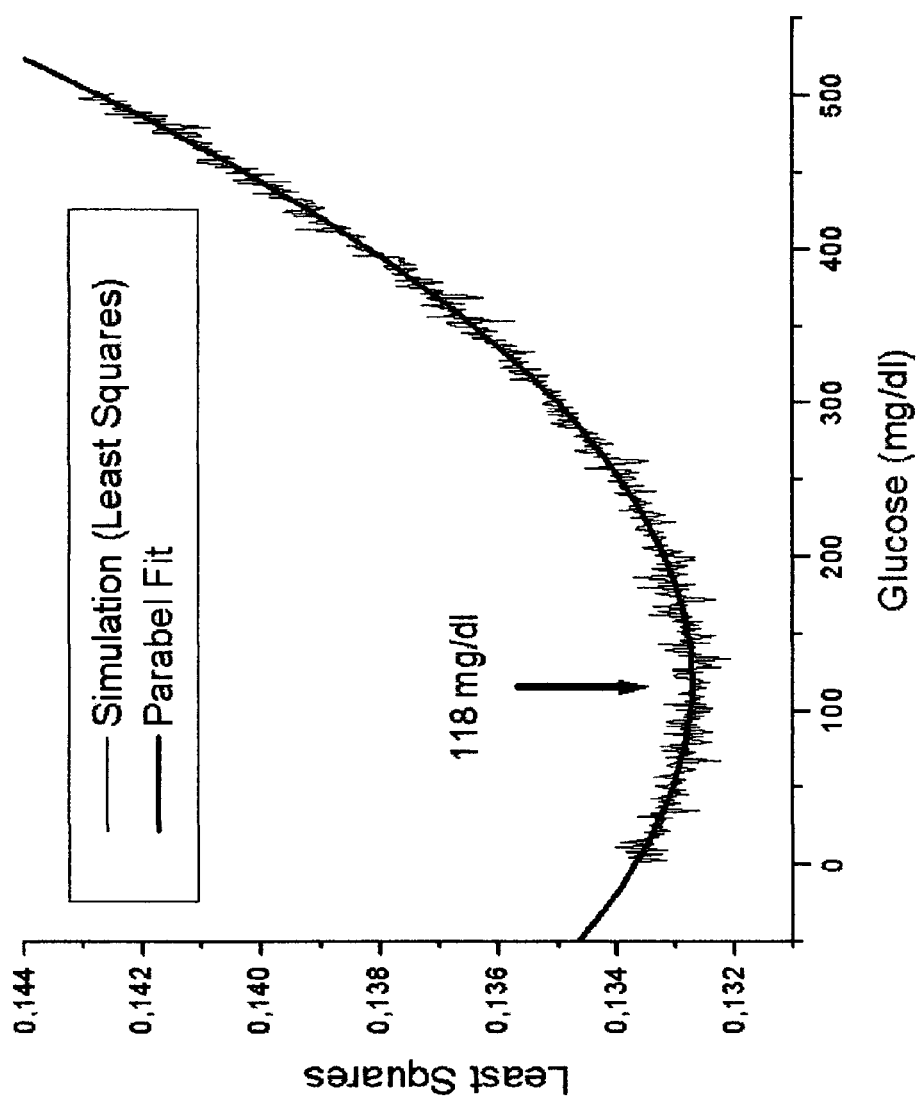
FIG. 9 depicts a simulated result of a measurement procedure.

Measurement Procedure:

After the calibration process equation (1) still shows only the unknown $conc_G$. The measurement procedure is analogous to the calibration process, wherein instead of the parameters $\theta_m$ and $const_{DB}$ the glucose concentration $conc_G$ is now systematically varied. The sum of the squared differences between $I_{meas}(\lambda)$ and $I_{sim}(\lambda)$ is again calculated for numerous individual measurements. FIG. 9 shows a simulated result of one such measurement procedure. Because of the fluctuating phase shift $\Delta\theta$, which was applied in this simulation with at most $\pm 1°$, clear fluctuations in the sums of the squared differences (least squares) are obtained. The sums of the squared differences can be approximated very well with a parabola fit in an averaged manner, as can be seen in FIG. 9. The position of the parabola minimum is subject to much smaller uncertainties than the absolute minimum of the fluctuating sum values. Upon repetition of the simulation the ascertained glucose concentration fluctuates from 118 mg/dl by merely approximately 1 mg/dl. In order to also be able to measure the concentrations of further optically active substances in the aqueous humour, equation (1) must be expanded by the corresponding term. In this case correspondingly more concentration values ($conc_G$, concLac, $conc_{Asc}$, $conc_{Am}$) must be systematically varied. Then in turn that combination of concentration values in which the sum of the squared differences or better of the fits matched to it has the minimal value is then again used as result.

The phase shifters 12 and 17 provided in the device according to the invention can be used to produce preferred polarization states at selected points. Thus it can for example be advantageous to produce s-polarized measurement radiation at the front of the lens of the eye with the phase shifter 12 in combination with the polarizer 11. This can be controlled via the radiation power reflected at the front of the lens of the eye which in this case is maximized and thus leads to smaller exposure times during measurement. It can furthermore be advantageous to create linearly polarized measurement radiation with the phase shifter 17 in front of the polarizer 18. Linearly polarized radiation represents a borderline case of elliptical polarization in which the principal axis of the polarization ellipse coincides with the linear polarization direction. If the optimum phase shifts for a person are known, then the variable phase shifter 12 and 17 can also be replaced by correspondingly adapted phase plates.

An optional constituent of the method according to the invention is also to animate the eye to perform artificial saccades with the help of the luminous display in the alignment device 29, by presenting the eye with a spatially varying fixing light in order to influence the value $\Delta\theta$ in targeted manner.

According to the invention the angle of incidence of the measurement radiation on the cornea can also be chosen individually or for the majority of eyes such that the corneal birefringence and thus the value $\theta_m$ are minimized.

The invention also claims all methods of the same procedure in which only a more or less precise model for describing the influencing of the polarization by the eye is taken as a basis than in equation (1). A refined model could for example also taken into account that small changes in the angle of incidence at the lens of the eye slightly influence the polarization state of the measurement radiation on the basis of the reflection process.

A main purpose of the invention is to deduce from the measured glucose concentration in the aqueous humour the glucose concentration in the blood (blood sugar level) correlated thereto. The invention can however for example also be used to ascertain the training condition of a sportsman or a patient from the measured lactate concentration in the aqueous humour. Furthermore the measured ascorbin concentration in the aqueous humour can be used to establish pathological changes to the eye.

The invention claimed is:

1. A device for determining concentrations of optically active substances in aqueous humour of an eye, comprising
a radiation source and a first polarizer adapted to radiate polarized incident measurement radiation into the eye, wherein the measurement radiation simultaneously or quasi-simultaneously covers a wavelength range of more than 100 nm;
a second polarizer that polarizes returned measurement radiation reflected by the lens of the eye linearly, circularly or elliptically,
and a spectrometric array that is oriented to receive and detect the polarized measurement radiation and configured to quantitatively record the returned measurement radiation as measurement values;
wherein reference radiation is split off between the radiation source and the second polarizer and received by a collecting optical element positioned and configured to collect the reference radiation that arises from interaction of measurement radiation with an optical interface of the cornea or wherein the reference radiation which is split off by a beam splitting optical element located and configured to direct a portion of the measurement radiation as the reference radiation to a collecting optical element; and
wherein the reference radiation is transmitted to the spectrometric array or to a second spectrometric array from the collecting optical element and wherein the spectrometric array or the second spectrometric array simultaneously or quasi-simultaneously spectrometrically resolves the reference radiation and provides resolved reference radiation data to a control unit wherein the control unit applies spectral intensity correction of measurement values of the spectrometric array based on the resolved reference radiation data.

2. The device according to claim 1 wherein measurement radiation simultaneously or quasi-simultaneously covers a wavelength range of more than 400 nm.

3. The device according to claim 1 wherein the optically active substance is selected from the group consisting of glucose, lactate and ascorbic acid.

4. The device according to claim 1, further comprising a variable or fixed phase shifter in front of the first polarizer.

5. The device according to claim 1, further comprising a variable or fixed phase shifter between the radiation source and the eye.

6. The device according to claim 1, wherein at least one of the first and second polarizer comprises a motor-driven turnable polarizer.

7. The device according to claim 1, further comprising actuators with which deflection mirrors are linearly shifted, the deflection mirrors deflecting at least one of the incident measurement radiation and the returned measurement radiation.

8. The device according to claim 1, further comprising deflection mirrors that are fixed or can be tilted manually or by motor, the deflection mirrors deflecting at least one of the incident measurement radiation and the returned measurement radiation.

9. The device according to claim 1, further comprising a luminous display, with which the eye is presented with a spatially varying fixation target in an alignment device.

10. The device according to claim 1, wherein the radiation source further comprises at least two LEDs of different centroid wavelength, whose radiation is directed into a joint beam path via at least one dichroitic beam splitter.

11. The device according to claim 1, wherein the radiation source further comprises an UV LED, a white-light LED, an LED in the red spectral range and an LED in the near infra-red spectral range.

12. The device according to claim 1, wherein the spectrometric array comprises a strongly dispersive prism or a grating.

13. The device according to claim 1, wherein the spectrometric array comprises a digital camera with 12 to 16-bit intensity resolution.

14. The device according to claim 1, further comprising a spatially-resolving optical detector with which the positioning of the device vis-à-vis the eye is controlled.

15. The device according to claim 1, further comprising a three-point attachment for positioning the measuring device against a head of a human.

16. The device according to claim 1, further comprising an OCT appliance for the geometric measurement of an anterior chamber of the eye.

* * * * *

UNITED STATES PATENT AND TRADEMARK OFFICE
CERTIFICATE OF CORRECTION

Page 1 of 1

PATENT NO. : 9,144,400 B2
APPLICATION NO. : 14/243594
DATED : September 29, 2015
INVENTOR(S) : Peter Westphal It is certified that error appears in the above-identified patent and that said Letters Patent is hereby corrected as shown below:

IN THE SPECIFICATION

Column 11, Line 44:
After "discrete" insert --$\lambda$--

Column 12, Line 53:
After "could" insert --,--
After "example" insert --,--

Column 12, Line 54:
Delete "taken" and insert --take--

Signed and Sealed this
Twenty-second Day of March, 2016

Michelle K. Lee
*Director of the United States Patent and Trademark Office*